United States Patent [19]

Gauthier

[11] 4,256,119
[45] Mar. 17, 1981

[54] BIOPSY NEEDLE

[75] Inventor: Thomas E. Gauthier, Rochester, Minn.

[73] Assignee: Gauthier Industries, Inc., Rochester, Minn.

[21] Appl. No.: 76,069

[22] Filed: Sep. 17, 1979

[51] Int. Cl.³ .............................................. A61B 10/00
[52] U.S. Cl. .................... 128/754; 128/310; 128/347
[58] Field of Search ............................. 128/751–754, 128/310, 347, DIG. 9, 218 C

[56] References Cited

U.S. PATENT DOCUMENTS

| 2,496,111 | 1/1950 | Turkel ................................ 128/754 |
| 2,516,492 | 7/1950 | Turkel ................................ 128/754 |
| 2,865,374 | 12/1958 | Brown et al. ..................... 128/347 X |
| 3,353,718 | 11/1967 | McLay .............................. 128/218 C |
| 3,598,108 | 8/1971 | Jamshidi et al. .................... 128/754 |
| 3,628,524 | 12/1971 | Jamshidi et al. .................... 128/754 |
| 3,630,192 | 12/1971 | Jamshidi et al. .................... 128/754 |

FOREIGN PATENT DOCUMENTS 949943  9/1949  France ................................. 128/347

*Primary Examiner*—Lee S. Cohen
*Attorney, Agent, or Firm*—Burd, Bartz & Gutenkauf

[57] ABSTRACT

A new improved biopsy needle for collecting animal specimens for examination. The biopsy needle includes an elongated hollow needle body having a handle secured to one end and a removable elongated stylet adapted to be positioned within the needle body and having a knob secured to one end adapted to be locked within the needle handle. The handle is characterized by an open loop or "C" configuration with the needle secured in the center of the closed side of the loop and with the stylet knob positioned between the free ends of the open side. The stylet is spring biased relative to the needle and handle and has projecting locking pins engageable with the free ends of the handle loop. The smooth top palm-engaging surface of the instrument makes the needle easier and more comfortable to use. The design permits attachment of a syringe to the needle body. The needle body and handle are secured together in a rigid joint in a unique manner.

11 Claims, 8 Drawing Figures

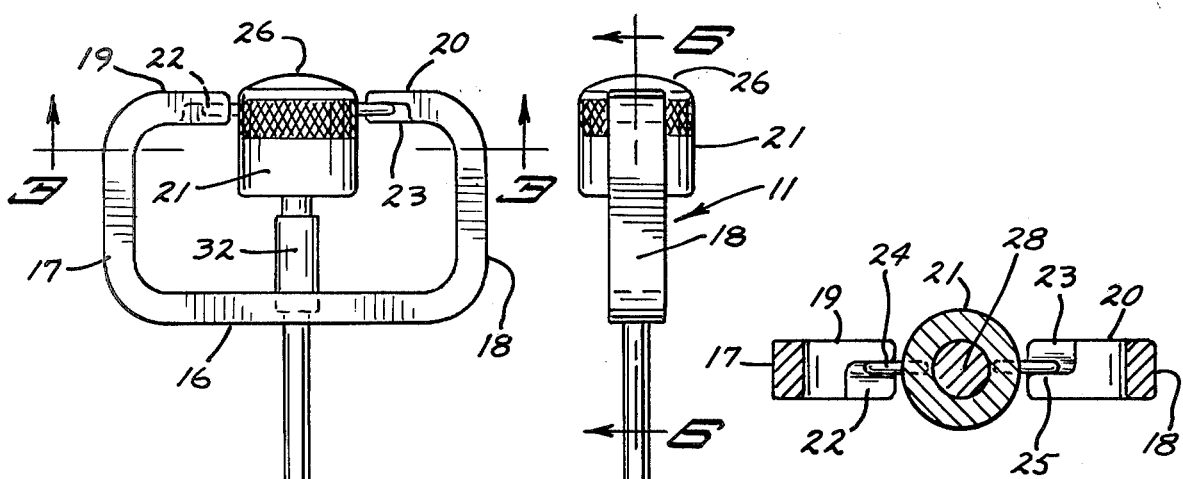
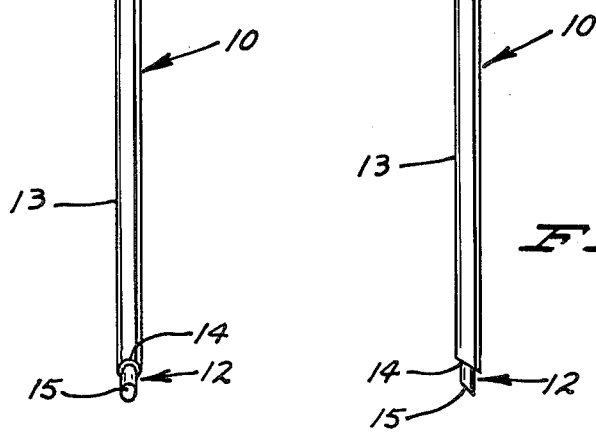
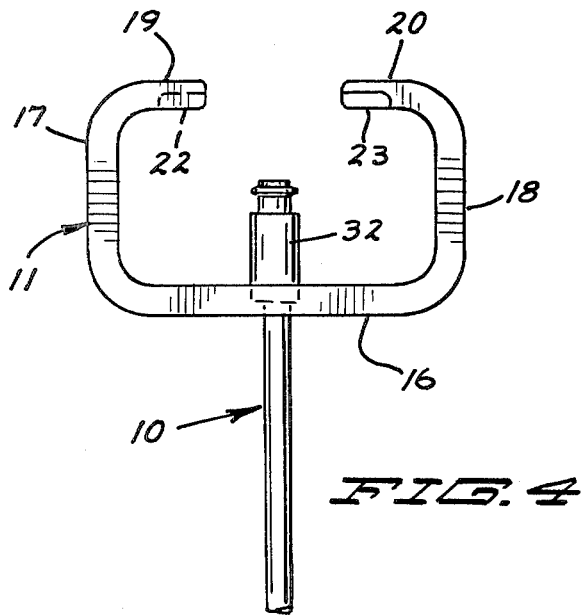
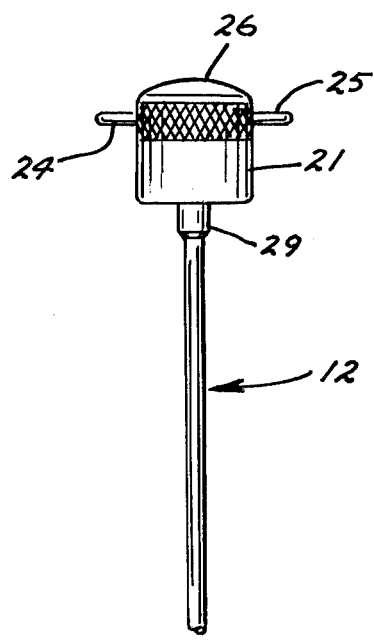

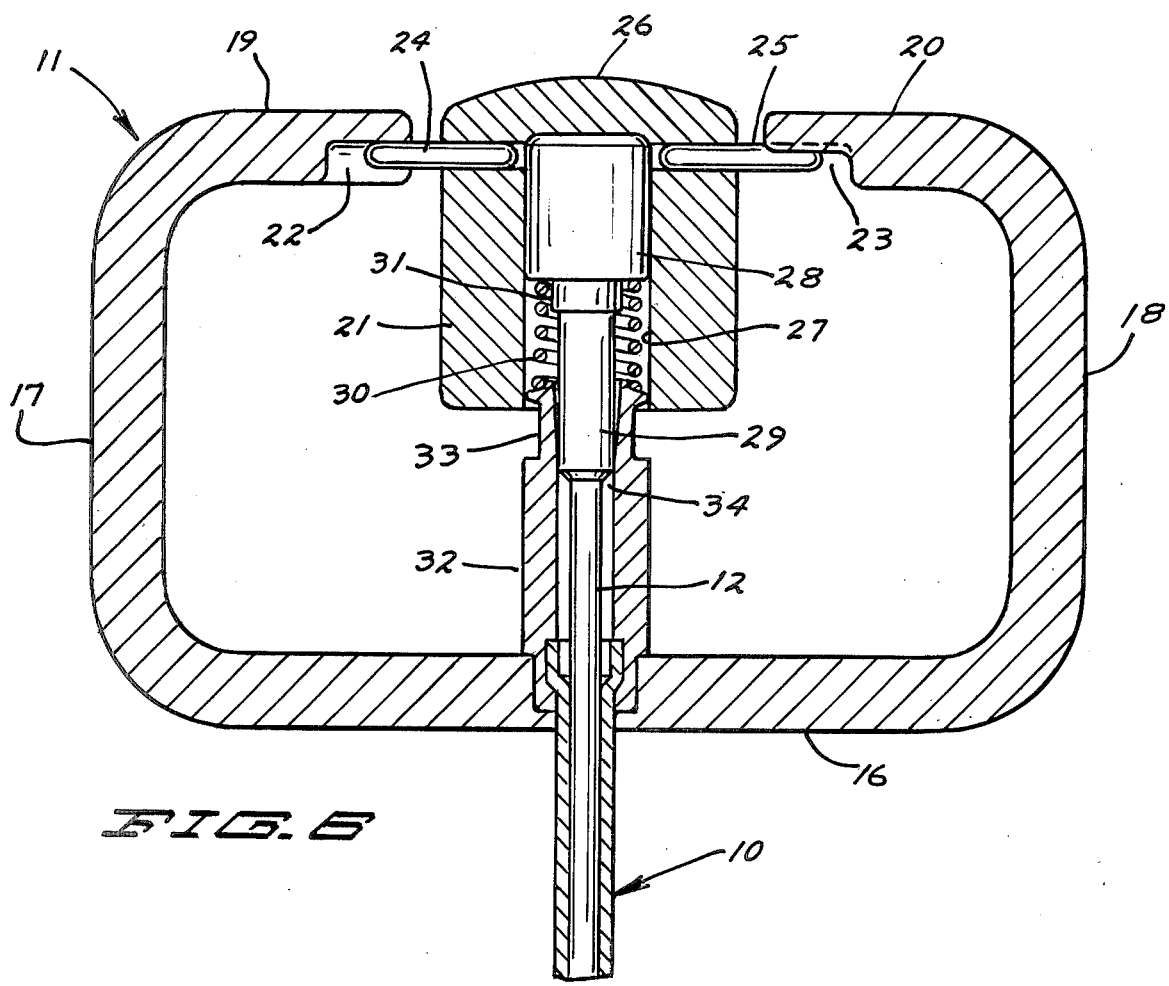
FIG. 6
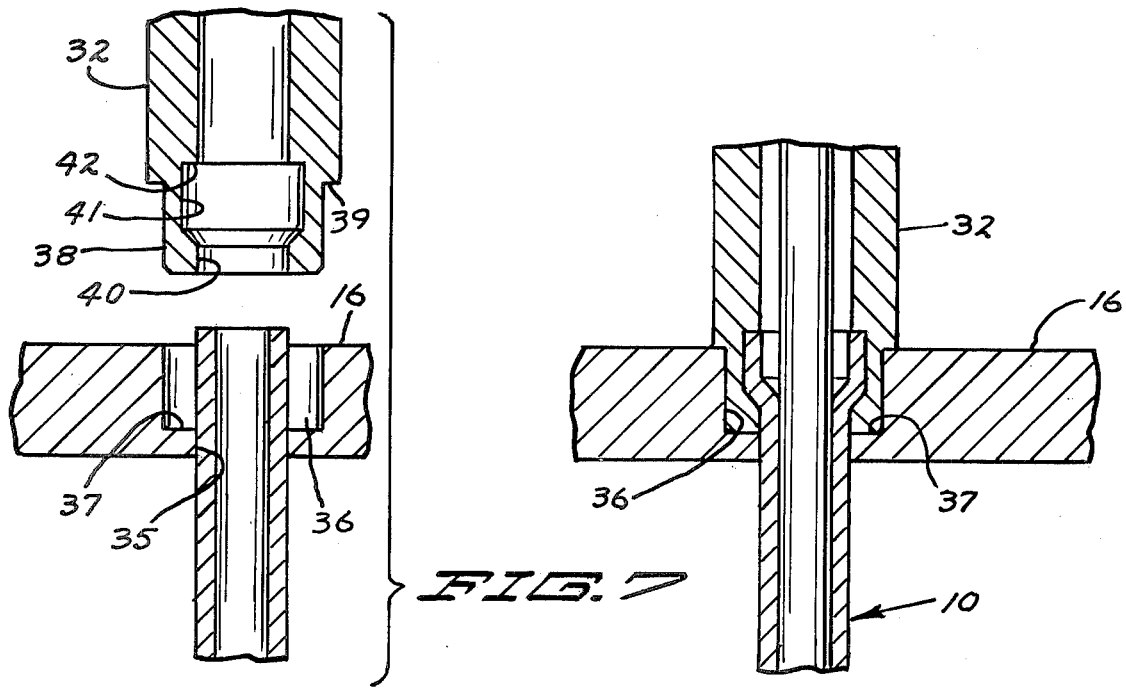
FIG. 7
FIG. 8

BIOPSY NEEDLE

BACKGROUND OF THE INVENTION

This invention is directed to a biopsy needle for collecting animal tissue specimens for pathological or other studies. More particularly, the invention is directed to a biopsy needle for use in obtaining bone marrow specimens.

THE PRIOR ART

A large number and variety of biopsy devices are available and in widespread use. Jamshidi U.S. Pat. No. 3,598,108 and No. 3,630,192 are exemplary of the types available. The biopsy needle described in Jamshidi U.S. Pat. No. 3,628,524 is exemplary of those especially adapted for obtaining bone marrow specimens. The biopsy devices of the prior art are subject to certain disadvantages. Among these are the design of the finger-gripping elements which make it difficult and uncomfortable to force the needle cutting surface to the desired site, the relative lack of control or "feel" as the needle penetrates the tissue, etc. The biopsy needle of the present invention is directed toward alleviating these disadvantages as well as to introduce advantages in the form of a better gripping handle, a stylet with a larger more comfortable pushing area, greater ease of locking and removing the stylet within the biopsy needle, ability to attach a syringe to the biopsy needle for aspiration of fluid from the biopsy site, and the like.

SUMMARY OF THE INVENTION

Broadly stated, the present invention is directed to a biopsy needle comprising an elongated hollow needle body, an elongated stylet positioned within the needle body, and having a knob secured to one end, a handle rigidly attached to one end of the needle body, and locking means for securing the stylet within the needle body. The handle is characterized by a transverse bar perpendicular to the longitudinal axis of the instrument, a pair of parallel spaced apart side bars extending upwardly from the ends of the transverse bar, and a pair of bar segments extending inwardly from the upper ends of the side bars, the inner free ends of these side bar segments being spaced apart to receive and lock in place the knob of the stylet. The knob of the stylet protrudes slightly beyond the handle means and is provided with a smooth palm-engaging surface making it easy and comfortable to insert the device. The stylet is spring biased for easy locking and unlocking and removal. The handle design permits attachment of a syringe to the needle body. The needle body and handle are secured together in a unique fashion.

BRIEF DESCRIPTION OF THE DRAWINGS

The invention is further illustrated by the accompanying drawings in which corresponding parts are identified by the same numerals, and in which:

FIG. 1 is a front elevation of the biopsy needle assembly according to the present invention;

FIG. 2 is a side elevation thereof;

FIG. 3 is a section on the line 3—3 of FIG. 1 and in the direction of the arrows;

FIG. 4 is a fragmentary front elevation of the needle body and handle with stylet removed;

FIG. 5 is a fragmentary front elevation of the stylet;

FIG. 6 is a fragmentary section on an enlarged scale on line 6—6 of FIG. 2 and showing details of construction of the needle and stylet;

FIG. 7 is a fragmentary section on an enlarged scale showing the manner in which the handle and needle body are secured together, the elements being shown in preassembled relation; and FIG. 8 is a similar fragmentary section on an enlarged scale showing the same elements assembled.

DETAILED DESCRIPTION OF THE PREFERRED EMBODIMENT

Referring now to the drawings, and particularly to FIGS. 1 and 2, there is shown a biopsy needle assembly according to the present invention and including a needle body indicated generally at 10, connected to a handle indicated generally at 11, and having a stylet indicated generally at 12 positioned within the needle body. The needle body is of generally uniform hollow cylindrical configuration throughout a major portion of its length, although preferably its distal end portion 13 is tapered toward the tip 14 in the manner shown and described in the aforesaid Jamshidi U.S. Pat. No. 3,628,524. The tip 14 is a cutting edge. It is preferably beveled as shown. The cutting edge may be serrated or saw-toothed if desired. The distal end of stylet 12 preferably protrudes a short distance, such as 1 to 3 mm from the cutting edge of the needle body and is provided with a beveled face 15 to form a penetrating edge.

The handle 11 includes a transverse bar portion 16 which extends perpendicular to the longitudinal axis of the needle and stylet. A pair of parallel spaced apart side bars 17 and 18 are integral with and extend upwardly from the opposite ends of transverse bar 16. A pair of top bar segments 19 and 20 are integral with and extend inwardly from the upper ends of side bars 17 and 18, respectively. The inner free ends of bar segments 19 and 20 are spaced apart a sufficient distance to receive a knob 21 to which the proximal end of stylet 12 is rigidly secured. It will be observed that the handle comprises a single metal bar or rod formed into the shape of an open loop having the configuration of a square block C laid on its side and embracing the stylet knob. Although shown as having a generally rectangular configuration, the open loop handle may alternatively be formed in a circular or ovoid configuration, in which case bars 16-18 and bar segments 19 and 20 will be arcuate.

A pair of recesses 22 and 23 are formed in the inside surfaces of the free ends of upper handle bar segments 19 and 20, as best seen in FIG. 3. Recess 22 enters from one side face of handle 22 and extends for about two-thirds of the width thereof, while recess 23 enters from the opposite face by about the same distance. Knob 21 is provided with a pair of locking elements, here shown as pins 24 and 25 pressed into suitable diametrically opposed holes in the upper portion of stylet knob 21. It will be noted that in locking position, pin 24 engages recess 22 and pin 25 engages recess 23. Because of the location of the locking recesses on the opposite faces of the handle, the pins and recesses are brought into locking engagement by rotation of the stylet.

The body of stylet knob 21 is of generally uniform cylindrical configuration. At least a portion of the cylindrical wall is desirably knurled to facilitate easy grasping between finger and thumb. It will be noted that when the stylet is in locked position, the top surface 26 of the stylet knob protrudes slightly above the top surface of handle bar segments 19 and 20. This is preferably in the form of a smooth large radius convex surface which, along with the top surface of the handle, provides a broad relatively large area which comfortably engages the palm of the hand when the handle is grasped with the fingers engaging the bottom surface of transverse bar 16.

To facilitate locking and unlocking of the stylet and easy removal from the needle body, the stylet is spring biased with respect to the needle body and handle. As seen in FIG. 6, stylet knob 21 has a deep central opening 27 in its bottom surface. Stylet 12 is press fit into one end of a mounting fitting or hub 28 which in turn is press fit into central opening 27. The length of stylet hub 28 is greater than the depth of opening 27 such that the bottommost end 29 projects beyond the bottommost surface of knob 21. The bottom end of hub 28 is of reduced diameter forming an annular recess with the wall of opening 27. A coil spring 30 is fit into this annular recess and is press fit on a shoulder 31 at the juncture between the upper and lower ends of stylet hub 28.

Needle mounting fitting or hub 32 serves in part to secure the needle body into the handle and projects upwardly from the transverse bar 16 of handle 11. The topmost end 33 of hub 32 is of a diameter which will fit into opening 27 in stylet knob 21 when the stylet is in locked position, as shown. The bottommost end of spring 30 engages the flanged top surface of hub 32, compressing the spring and maintaining the knob and stylet in rigid spring biased locked position in the needle and hand. The uppermost end of the tubular passage within needle hub 32 is enlarged to accommodate the projecting bottommost end of stylet hub 29. This passage 34 is preferably tapered, as a Luer taper, to receive the tip or nozzle of a syringe so as to permit the aspiration of fluid through the needle to the biopsy site when the stylet is not in place. The flange at the top of hub 32 is preferably a Luer lock connection.

The method of assembly of the needle hub and handle is best seen by comparison of FIGS. 7 and 8. Transverse handle bar 16 has a central opening 35 which is of enlarged diameter 36 in the inner surface of bar 16 forming a shoulder 37. The proximal end of the needle body is initially of hollow uniform cylindrical configuration of a diameter to fit with a tight slide fit into the reduced diameter portion of opening 35. The needle body is initially inserted through opening 35 until the end of the needle projects slightly above the top surface of bar 16. The bottommost end 38 of hub 32 is of reduced diameter corresponding to the diameter of enlarged opening 36 and of a length corresponding to the depth of opening 36 forming a shoulder 39 adapted to engage the inside surface of transverse bar 16 as the bottommost end of the hub engages shoulder 37 in the central opening.

The central passage through needle hub 32 is of enlarged diameter at its bottommost end 40 corresponding to the outside diameter of the needle body. The central passage immediately inwardly from opening 40 is of further increased diameter forming a circular recess 41 having a shoulder 42 formed with the remainder of the central passage. The proximal end of the needle is forced through passage 40 into recess 41 until it is approximately parallel to shoulder 42. Then, with the bottommost end of the hub 32 engaging shoulder 37 and shoulder 39 engaging the inside surface of the handle, a tool is introduced through the hub central passage to deform the proximal end of the needle body enlarging it and forcing its outer surface into engagement with the surface of hub recess 41. A tight rigid sealed joint is thus formed. The joint should preferably be further sealed and strengthened by the application of silver solder, or the like.

The expressions "top", "upper", "bottom", "lower", and the like, are used in a relative sense only. References to "top" and the like refer to the proximal direction, and references to "bottom" and the like refer to the distal direction.

The biopsy needle according to the present invention is used in the conventional manner. With the stylet locked in place and with the handle grasped between fingers and palm, the stylet and/or needle tip are inserted through an incision in the body and gently forced through the tissue and/or bone to the biopsy site. The stylet is then withdrawn by depressing the knob slightly against the tension of spring 30 to release the locking pins from the locking notches. Then, slight rotation of the knob permits the stylet to be withdrawn. The needle is inserted further, forcing a core of the desired biopsy specimen up into the needle body. The needle is withdrawn and by insertion of the stylet into the needle tip, the biopsy specimen is dislodged from the needle for examination.

The biopsy needle of this invention is intended for reuse. It is preferably constructed from high strength, long-life material, bio-compatible, non-toxic to body tissues, readily sterilizable, and the like, such as surgical grades of stainless steel, or the like. Although especially adapted for collecting bone marrow specimens, the needle may be used to obtain specimens from other sites such as the kidney, spleen, liver, muscle, skin, and other tissues.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A biopsy needle comprising:
   (A) an elongated hollow needle body having proximal and distal ends, said body being open at each end, and the distal end defining a cutting edge,
   (B) an elongated stylet having proximal and distal ends positioned within said needle body with distal ends adjacent,
      (1) the distal end of said stylet defining a penetrating edge, and
      (2) a knob having proximal side and distal side surfaces rigidly attached to the proximal end of the stylet,
   (C) an open loop handle rigidly attached to the proximal end of said needle body, said handle comprising:
      (1) a transverse bar disposed generally perpendicular to the longitudinal axis of said needle body and stylet,
      (2) a pair of spaced apart side bars extending upwardly in the proximal direction from the ends of said transverse bar, and
      (3) a pair of upper bar segments having proximal side and distal side surfaces extending inwardly from the upper ends of said side bars toward the longitudinal axis extending through the needle body, the inner ends of said bar segments being spaced apart to receive the knob of the stylet, and (D) locking means for securing said stylet within the needle body and handle and comprising:
  (1) a pair of locking elements extending radially from the opposite sides of the stylet knob, and
  (2) a pair of recesses in the inside distal side surfaces of the spaced apart ends of the upper handle bar segments engageable with said locking elements.

2. A biopsy needle according to claim 1 wherein said needle body is of generally uniform hollow cylindrical configuration throughout a major portion of its length and the distal end portion is tapered toward the tip.

3. A biopsy needle according to claim 1 wherein said stylet is of generally uniform cylindrical configuration.

4. A biopsy needle according to claim 1 wherein the distal end of said stylet protrudes a short distance beyond the distal end of the needle body.

5. A biopsy needle according to claim 1 wherein said stylet knob is of generally uniform cylindrical configuration with a large radius smooth convex palm-engaging proximal side surface protruding above the proximal side surfaces of said upper handle bar segments.

6. A biopsy needle according to claim 1 wherein:
  (A) the proximal end of said needle body extends through a central opening in the transverse bar of the handle, and
  (B) a hollow hub having proximal and distal ends engages said proximal end of the needle body and said opening to rigidly secure the needle body therein.

7. A biopsy needle according to claim 6 wherein:
  (A) the distal end of said hub has a circular recess therein coaxial with the longitudinal axis of the needle body, having a diameter greater than the diameter of the needle body and an opening of substantially the same diameter as the outside diameter of the needle body, and
  (B) the proximal end of the needle body is expanded into engagement with the wall of said recess.

8. A biopsy needle according to claim 6 wherein the proximal end of said needle body hub has a tapered coaxial channel therein adapted for engagement with a syringe.

9. A biopsy needle according to claim 8 wherein said channel is a Luer taper and said hub is provided with a Luer lock connection.

10. A biopsy needle according to claim 6 wherein:
  (A) said stylet knob has a central opening in its distal side surface,
  (B) said stylet has a hub at its proximal end, said hub having proximal and distal ends,
    (1) the proximal end of said hub engaging said central knob opening,
    (2) the distal end of said hub being of reduced diameter and projecting beyond the distal side surface of the knob,
  (C) an annular recess in the knob central opening around the distal end of the stylet hub, and
  (D) a coil spring within said annular recess,
    (1) said spring having proximal and distal ends, and
    (2) the distal end of said spring being engageable with the proximal end of the needle body hub to spring bias the stylet for engagement and disengagement of the locking means.

11. A biopsy needle according to claim 1 wherein said locking elements are pins.

* * * * *